(12) United States Patent
Ganmukhi et al.

(10) Patent No.: US 11,355,119 B2
(45) Date of Patent: Jun. 7, 2022

(54) SYSTEMS AND METHODS FOR VOICE ASSISTANT FOR ELECTRONIC HEALTH RECORDS

(71) Applicant: Bola Technologies, Inc., Boston, MA (US)

(72) Inventors: Rushi M. Ganmukhi, Boston, MA (US); Daniel Brownwood, Boston, MA (US); Sidharth Malhotra, Boston, MA (US); Augusto Monteiro Nobre Amanco, Ceará (BR)

(73) Assignee: Bola Technologies, Inc, Boston, MA (US)

( * ) Notice: Subject to any disclaimer, the term of this patent is extended or adjusted under 35 U.S.C. 154(b) by 0 days.

(21) Appl. No.: 17/383,723

(22) Filed: Jul. 23, 2021

(65) Prior Publication Data
US 2022/0028382 A1 Jan. 27, 2022

Related U.S. Application Data

(60) Provisional application No. 63/056,258, filed on Jul. 24, 2020.

(51) Int. Cl.
*G10L 15/22* (2006.01)
*G16H 10/60* (2018.01)
*G10L 15/18* (2013.01)
*G10L 15/06* (2013.01)

(52) U.S. Cl.
CPC .......... *G10L 15/22* (2013.01); *G10L 15/063* (2013.01); *G10L 15/18* (2013.01); *G16H 10/60* (2018.01); *G10L 2015/223* (2013.01); *G10L 2015/225* (2013.01)

(58) Field of Classification Search
None
See application file for complete search history.

(56) References Cited

U.S. PATENT DOCUMENTS

| | | | |
|---|---|---|---|
| 6,434,547 B1* | 8/2002 | Mishelevich | G10L 15/26 |
| 9,585,549 B1* | 3/2017 | Elazar | A61B 1/00009 |
| 10,748,650 B1* | 8/2020 | Ricci | G16H 30/40 |
| 2003/0154085 A1* | 8/2003 | Kelley | G06F 40/174 |
| | | | 704/E15.045 |
| 2007/0129969 A1* | 6/2007 | Burdick | G16H 10/60 |
| | | | 705/3 |
| 2009/0177495 A1* | 7/2009 | Abousy | G16H 40/67 |
| | | | 705/3 |
| 2009/0276223 A1* | 11/2009 | Jaiswal | G10L 17/00 |
| | | | 704/E15.005 |
| 2010/0088095 A1* | 4/2010 | John | G10L 15/22 |
| | | | 704/235 |
| 2010/0121658 A1* | 5/2010 | Kaminski | A61C 19/00 |
| | | | 715/790 |
| 2010/0299135 A1* | 11/2010 | Fritsch | G06F 40/30 |
| | | | 704/E15.044 |
| 2011/0066634 A1* | 3/2011 | Phillips | G10L 15/22 |
| | | | 707/769 |

(Continued)

*Primary Examiner* — Jonathan C Kim
(74) *Attorney, Agent, or Firm* — Foley & Lardner LLP

(57) ABSTRACT

An electronic record voice assistant system can include one or more processors that receive audio data, apply a machine learning model to the audio data to generate speech data including at least one value, determine a state of an electronic record, and update one or more fields of the electronic record using the state and the at least one value.

20 Claims, 5 Drawing Sheets

(56) References Cited

U.S. PATENT DOCUMENTS

| | | | | |
|---|---|---|---|---|
| 2012/0323574 A1* | 12/2012 | Wang | ............... | G16H 10/60 |
| | | | | 704/254 |
| 2013/0308839 A1* | 11/2013 | Taylor | ............... | G16H 30/20 |
| | | | | 382/128 |
| 2014/0019128 A1* | 1/2014 | Riskin | ............... | G16H 15/00 |
| | | | | 704/235 |
| 2014/0136196 A1* | 5/2014 | Wu | ............... | G10L 15/22 |
| | | | | 704/235 |
| 2015/0379241 A1* | 12/2015 | Furst | ............... | G16H 10/60 |
| | | | | 705/3 |
| 2016/0055321 A1* | 2/2016 | Acharya | ............... | G16H 30/20 |
| | | | | 705/3 |
| 2016/0300573 A1* | 10/2016 | Carbune | ............... | G10L 17/22 |
| 2017/0147751 A1* | 5/2017 | Schwartz | ............... | G16Z 99/00 |
| 2017/0235879 A1* | 8/2017 | Sohn | ............... | H04N 5/23229 |
| | | | | 705/2 |
| 2018/0130558 A1* | 5/2018 | Kaminski | ............... | A61C 19/00 |
| 2019/0043607 A1* | 2/2019 | Sears | ............... | G16H 30/20 |
| 2019/0304582 A1* | 10/2019 | Blumenthal | ............... | G16H 40/67 |
| 2019/0304604 A1* | 10/2019 | Kupersmith | ............... | G06F 40/205 |
| 2019/0333644 A1* | 10/2019 | Lamarre | ............... | G16H 10/60 |
| 2020/0321087 A1* | 10/2020 | Willis | ............... | G16H 70/00 |
| 2020/0350072 A1* | 11/2020 | McEwing | ............... | G16H 50/70 |
| 2022/0028382 A1* | 1/2022 | Ganmukhi | ............... | G10L 15/22 |
| 2022/0044812 A1* | 2/2022 | Barnes | ............... | G16H 10/60 |

* cited by examiner

FIG. 1

SYSTEMS AND METHODS FOR VOICE ASSISTANT FOR ELECTRONIC HEALTH RECORDS

CROSS-REFERENCE TO RELATED APPLICATIONS

The present application claims the benefit of priority to U.S. Provisional Application No. 63/056,258, filed Jul. 24, 2020, the disclosure of which is incorporated herein by reference in its entirety.

BACKGROUND

The present disclosure relates generally to the field of electronic record technology, and more particularly to systems and methods for voice assistants for electronic health records.

Electronic health record technology, including but not limited to practice management software, practice management systems (PMs), electronic health records (EHRs), electronic medical records (EMRs), and electronic dental records, can be used to maintain information regarding patients for subsequent retrieval and analysis. The information may be provided through various user interfaces in order to be stored in the electronic health record.

SUMMARY

At least one aspect relates to a system. The system can include one or more processors that receive audio data, apply a machine learning model to the audio data to generate speech data including at least one value, determine a state of an electronic record, and update one or more fields of the electronic record using the state and the at least one value. At least one command can be determined (e.g., inferred) based on the speech data or the at least one value, and used to update the one or more fields.

At least one aspect relates to a method. The method can include receiving an audio input indicating a command, pre-processing the audio input to generate audio data, generating text data by applying a speech model to the audio data, generating at least one value from the text data, determining a state of an electronic record, and updating the electronic record using the at least one value based on the state.

At least one aspect relates to a method of using voice commands to update electronic dental records. The method can include receiving, by one or more processors, audio data; applying, by the one or more processors, a speech model to the audio data to generate speech data including at least one value; determining, by the one or more processors, a state of a periodontal chart data object, the periodontal chart data object including a plurality of fields, each field associated with a tooth of a subject and at least one feature of the tooth, the state corresponding to a particular field of the plurality of fields; determining, by the one or more processors, a command based on at least one of the speech data or the at least one value; and assigning, by the one or more processors, the at least one value to the at least one feature of the tooth based on the command and the state.

In some implementations, assigning, by the one or more processors, the at least one value includes identifying the field with which the at least one feature is associated using the state.

In some implementations, the method includes updating, by the one or more processors, the state responsive to assigning the at least one value.

In some implementations, the method includes identifying, by the one or more processors, the particular field using the command.

In some implementations, the one or more processors include a first processor operating on a client device and a second processor operating on a server device.

In some implementations, generating the speech data includes using, by the one or more processors, the state as an input to the speech model.

In some implementations, assigning the at least one value includes accessing, by the one or more processors, an application providing an interface to the electronic record; and providing, by the one or more processors, the at least one value to the interface for assignment to the particular field.

In some implementations, the method includes validating, by the one or more processors, the at least one value by comparing the at least one value with an expected value and outputting an error responsive to the comparison not satisfying a comparison condition.

In some implementations, the method includes receiving, by the one or more processors, data indicative of a treatment plan, and assigning the data indicative of the treatment plan to an unstructured field of an electronic dental record that includes the periodontal chart data object.

In some implementations, the method includes providing, by the one or more processors, a feedback output regarding the assignment of the at least one value to the at least one feature of the tooth.

In some implementations, the at least one value includes a first value and a second value subsequent to the first value, and generating the at least one value includes generating the first value subsequent to generating the second value.

In some implementations, the method includes outputting, by the one or more processors using a client device, a request for a predetermined word; receiving, by the one or more processors, audio data expected to represent the predetermined word; and outputting, by the one or more processors, an error condition responsive to determining that the audio data expected to represent the predetermined word does not match the predetermined word.

In some implementations, a system can include one or more processors configured to receive audio data; apply a speech model to the audio data to generate speech data including at least one value; determine a state of a periodontal chart data object, the periodontal chart data object including a plurality of fields, each field associated with a tooth of a subject and at least one feature of the tooth, the state corresponding to a particular field of the plurality of fields; determine a command based on at least one of the speech data or the at least one value; and assign the at least one value to the at least one feature of the tooth based on the command and the state.

In some implementations, the one or more processors are configured to assign the at least one value by identifying the field with which the at least one feature is associated using the state.

In some implementations, the one or more processors are configured to update the state responsive to assigning the at least one value.

In some implementations, the one or more processors are configured to identify the particular field using the command."

In some implementations, the one or more processors include a first processor operating on a client device and a second processor operating on a server device.

In some implementations, the one or more processors are configured to apply the state as an input to the speech model.

In some implementations, the one or more processors are configured to assign the at least one value by accessing an application providing an interface to the electronic record; and providing the at least one value to the interface for assignment to the particular field.

In some implementations, the one or more processors are configured to validate the at least one value by comparing the at least one value with an expected value and outputting an error responsive to the comparison not satisfying a comparison condition.

At least one aspect relates to a method of integrating an electronic voice assistant with electronic records. The method can include receiving, by one or more processors, audio data; applying, by the one or more processors, a speech model to the audio data to generate speech data including at least one value; determining, by the one or more processors, a state of an electronic record, the electronic record including a plurality of fields; determining, by the one or more processors, a command based on at least one of the speech data or the at least one value; identifying, by the one or more processors, a particular field of the plurality of fields based on the state; and assigning, by the one or more processors, the at least one value to the particular field based on the command and the state.

In some implementations, the method includes updating, by the one or more processors, the state responsive to assigning the at least one value.

In some implementations, the method includes identifying, by the one or more processors, the particular field using the command.

In some implementations, the method includes applying, by the one or more processors, at least one of text recognition or computer vision to an image representing the electronic record to determine the state.

In some implementations, the method includes generating a data object representing the electronic record responsive to applying the least one of text recognition or computer vision to the image.

In some implementations, the method includes applying, by the one or more processors, a signal indicative of at least one of a mouse movement or a keystroke to a client device to assign the at least one value to the particular field.

In some implementations, the one or more processors include a first processor operating on a client device and a second processor operating on a server device.

In some implementations, the method includes applying, by the one or more processors, the state as input to the speech model.

In some implementations, the method includes determining, by the one or more processors, that the at least one value corresponds to unstructured data and assigning the unstructured data to an unstructured data field of the electronic record.

In some implementations, the electronic record includes at least one of an electronic health record, an electronic medical record, an electronic dental record, a customer relationship management record, or an enterprise resource planning record.

At least one aspect relates to a system. The system can include one or more processors configured to receive audio data; apply a speech model to the audio data to generate speech data including at least one value; determine a state of an electronic record, the electronic record including a plurality of fields; determine a command based on at least one of the speech data or the at least one value; identify a particular field of the plurality of fields based on the state; and assign the at least one value to the particular field based on the command and the state.

In some implementations, the one or more processors are configured to update the state responsive to assigning the at least one value.

In some implementations, the one or more processors are configured to identify the particular field using the command.

In some implementations, the one or more processors are configured to apply at least one of text recognition or computer vision to an image representing the electronic record to determine the state.

In some implementations, the one or more processors are configured to generate a data object representing the electronic record responsive to applying the least one of text recognition or computer vision to the image.

In some implementations, the one or more processors are configured to apply a signal indicative of at least one of a mouse movement or a keystroke to a client device to assign the at least one value to the particular field.

In some implementations, the one or more processors include a first processor operating on a client device and a second processor operating on a server device.

In some implementations, the one or more processors are configured to apply the state as input to the speech model.

In some implementations, the one or more processors are configured to determine that the at least one value corresponds to unstructured data and assign the unstructured data to an unstructured data field of the electronic record.

In some implementations, the electronic record includes at least one of an electronic health record, an electronic medical record, an electronic dental record, a customer relationship management record, or an enterprise resource planning record.

These and other aspects and implementations are discussed in detail below. The foregoing information and the following detailed description include illustrative examples of various aspects and implementations, and provide an overview or framework for understanding the nature and character of the claimed aspects and implementations. The drawings provide illustration and a further understanding of the various aspects and implementations, and are incorporated in and constitute a part of this specification.

BRIEF DESCRIPTION OF THE DRAWINGS

The accompanying drawings are not intended to be drawn to scale. Like reference numbers and designations in the various drawings indicate like elements. For purposes of clarity, not every component can be labeled in every drawing. In the drawings:

FIG. 1 depicts an example of an electronic health record.

DETAILED DESCRIPTION

Figure 2:
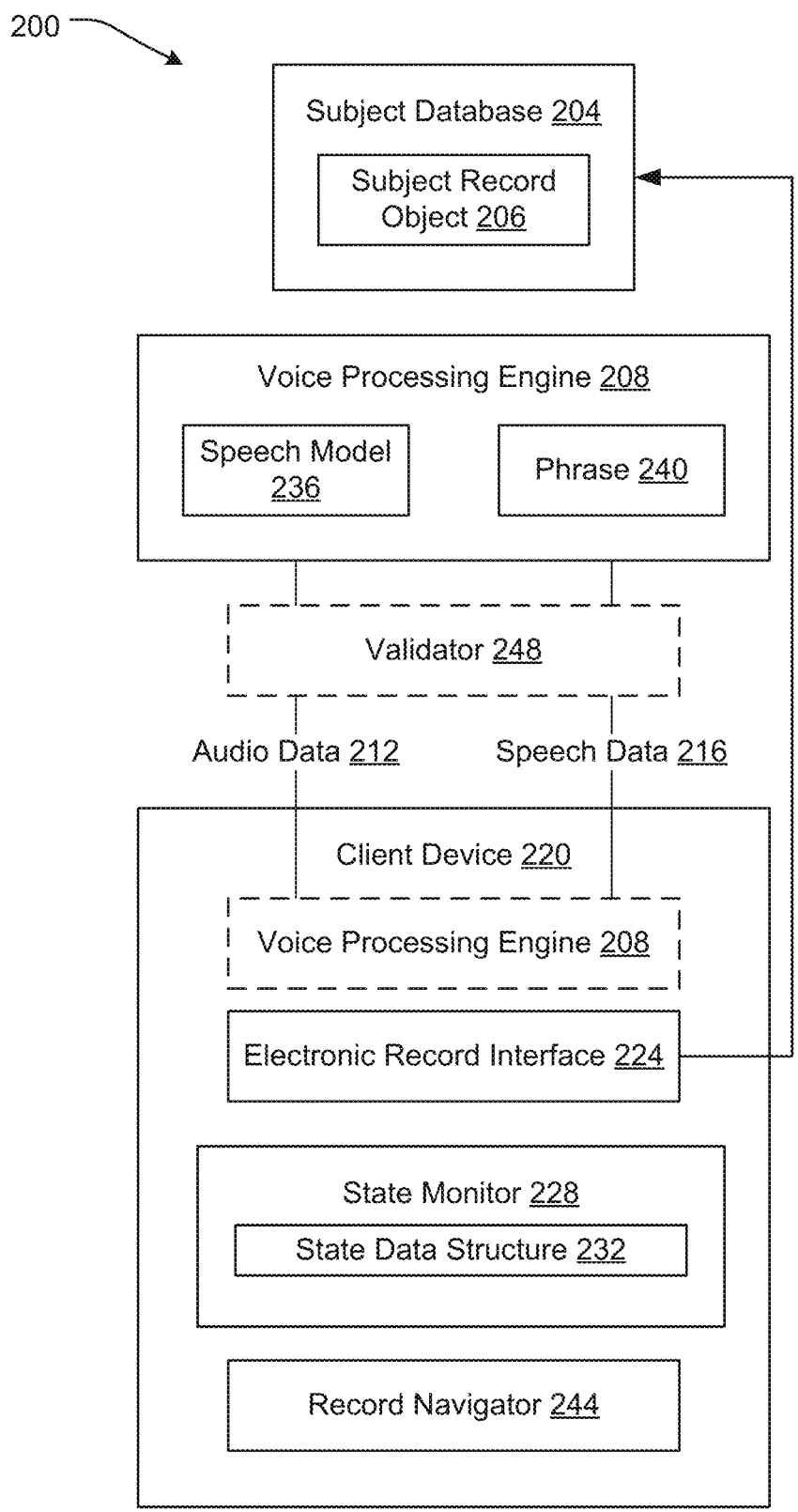
FIG. 2 depicts a block diagram of an example of an electronic record voice assistant system.

Electronic health record technologies, such as for medical and dental databases (e.g., practice management software, electronic dental records, PMs, EMRs, EHRs), can be updated using information received through various user interfaces. For example, a client device can operate an application or a browser-based interface that can receive subject data regarding a subject or patient. Providing the subject data during a procedure may require either a single user to break a sterile field and expend relatively large amounts of time both performing the procedure and provide the subject data or multiple users to both perform the procedure and provide the subject data, for the procedure to be interrupted to provide the subject data, or for the subject data to be provided subsequent to the procedure, which may increase an error rate associated with the subject data. Such records and databases can include or operate with electronic medical records, electronic dental records, practice management systems, treatment planning, and patient charting software. Such records and databases can also include or operate with customer relationship management (CRM) and enterprise resource planning (ERP) technologies.

Electronic tools, such as voice assistants, can receive the subject data in order to provide the subject data to the database. However, it can be difficult to accurately detect the subject data from speech provide to the voice assistant. It can also be difficult for a computer program to automatically and accurately navigate the user interface that receives the subject data.

Systems and methods in accordance with the present disclosure can enable a voice assistant to accurately process received audio in order to detect speech, including subject data and commands associated with the subject data, improve the speech models used for the speech detection, and accurately navigate the user interface to assign subject data to appropriate fields in the user database. This can enable electronic records to be accurately updated without requiring a user to take actions in both a sterile field (e.g., while in contact with a subject) and a non-sterile field (e.g., while in contact with a computing device). Systems and methods as described herein can enable more accurate and timely assignment of data (through user interfaces) to appropriate fields in databases including but not limited to PM, EHR, EMR, electronic dental record, CRM, and ERP databases. For example, a state of an electronic data record to which data is to be assigned can be monitored and validated based on the data being provided for assignment (e.g., with or without user input that confirms the state information).

As described further herein, systems and methods in accordance with the present disclosure can accurately provide inputs to and read information from a user interface of an application (e.g., front-end application) connected with the database (e.g., backend database), facilitating the ability to update the database and monitor state information without requiring a user to manually interact with the client device that presents the user interface or break a sterile field. For example, the system can use computer vision or other image processing algorithms to detect state, value, and configuration information of the user interface (e.g., read text data presented on the user interface). The system can use input entry processes such as robotic process automation (e.g., mimicking of keystrokes and mouse clicks) to provide inputs to the database through the user interface and the application. For example, the system can determine, from the speech data, a numerical phrase such as "1, 2, 3," and provide keystrokes or mouseclicks corresponding to entering the values 1, 2, 3 to the user interface. As such, the application, responsive to receiving the inputs from the system, can update the database and the user interface to present information corresponding to the values (e.g., as if a user had manually entered the values).

Figure 1:
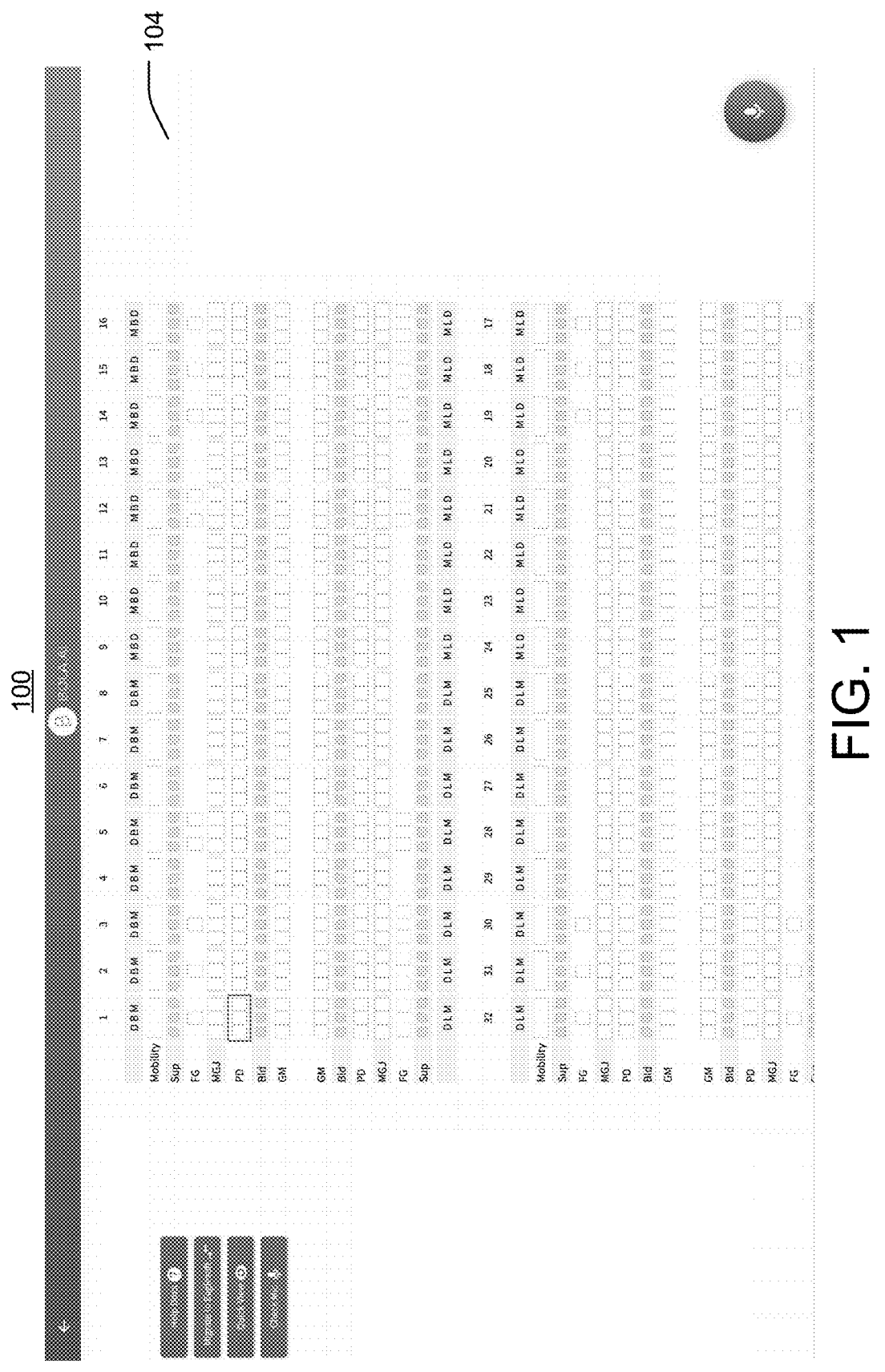

FIG. 1 depicts an example of a representation of an electronic record 100. The electronic record 100 can be a record object of a database, including but not limited to a database for practice management software, PMs, EHRs, EMRs, electronic dental records, CRM, and ERP technologies. The electronic record 100 can include a plurality of fields to which data can be assigned. Each electronic record 100 can be associated with a subject, such as a patient (including but not limited to an event associated with the subject, such as a treatment, procedure, or other interaction, such as a meeting or call). The electronic record 100 can include data from multiple points in time (e.g., to maintain longitudinal data regarding the subject). For example, the electronic record 100 can include data recorded from multiple events in which a subject undergoes a procedure or other medical or dental interaction. The electronic record 100 can include or receive at least one of structured data (e.g., data expected to be assigned to particular respective fields) or unstructured data (e.g., data corresponding to streams of text that can be assigned to various fields).

The electronic record 100 can be presented using a client device, and can receive subject data using a user interface of the client device. The client device can maintain at least a portion of the electronic record 100. The electronic record 100 can be maintained by a server device remote from the client device, and the client device can communicate the subject data to the server device to update the electronic record 100. The electronic record 100 can be maintained by an application native to one or more client devices (e.g., without the use of a server, such as by implementing the electronic record 100 and the user interface on a single client device, or implementing the electronic record 100 on a first client device (e.g., desktop computer) and the user interface on a second client device (e.g., portable electronic device), among other configurations).

As depicted in FIG. 1, the electronic record 100 can include a periodontal chart data object 104. The periodontal chart data object 104 can include structured data, such as fields associated with teeth of the subject and features of the teeth. The periodontal chart data object 104 can have values assigned to the fields responsive to receiving the subject data. For example, the periodontal chart object 104 can be used for a periodontal charting procedure in which a user, such as a dental hygienist, measures health of gums (e.g., using a probe to measure gum depths and other various of each tooth, which may include taking around 400 measurements in ten minutes). For example, periodontal values such as pocket depths, bleeding points, gingival margin/recession, suppuration, mucogingival junction, furcation, and mobility, among others, can be entered. Values can be assigned to a current tooth (e.g., bleeding on all sides, bleeding on mesial side, gingival margin with 323), other teeth (e.g., bleeding on tooth 3 all, gingival margin tooth number 10 with 323), multiple teeth (bleeding sextant one, repeat 010 on tooth number 10 to tooth number 16), and various combinations thereof. Commands to navigate the electronic record 100 can be provided, such as jump, go to, move, skip, go back, or undo.

FIG. 2 depicts an example of an electronic record voice assistant system 200 (hereinafter referred to as system 200). The system 200 and components thereof can be implemented using various features of the computing environment 400 described with reference to FIGS. 4A-4B. Various components of the system 200 can be implemented using one or more computing devices; for example, the subject database 204 can be implemented using one or more first servers, and the voice processing engine 208 can be implemented using one or more second servers (or by a native application operating on a desktop client that implements a native application for the electronic record). Various aspects of the system can be implemented as a web browser or extension (e.g., if the electronic record is accessed through a web-based interface) or as a desktop application (e.g., if the software associated with the electronic record is a native application). The system 200 can be fully integrated into the electronic record 100 (e.g., as a single application in which the system 200 includes the electronic record 100 and/or a database that includes the electronic record 100).

The system 200 can use voice commands to control web-based and native electronic health records, including by identifying user inputs (e.g., commands) programmatically and manipulating interfaces that present the electronic health records based on the commands. The system 200 can be used for various medical and dental electronic records, such as for periodontal charting, tooth/restorative charting, electronic health record navigation, treatment planning, transcribing clinical notes from speech data, and messaging between operators. The system 200 can be used to detect and implement the various commands and record value updates described with reference to the electronic record 100 of FIG. 1. The system 200 can be used to retrieve and assign structured data from sales or support calls or meetings for CRM databases (e.g., from a recording of a call or meeting from which audio data can be retrieved). The system 200 can be used to retrieve and assign structured data such as notes into an ERP database (e.g., notes dictated by a mechanic).

The system 200 can include a subject database 204. The subject database 204 can store and maintain record objects 206 for various subjects. The record objects 206 can include the electronic record 100 and features thereof described with reference to FIG. 1. The record objects 206 can include subject profile data, such as name, age or date of birth, height, weight, sex, and medical history information.

The system 200 can include a voice processing engine 208. Briefly, the voice processing engine 208 can receive audio data 212 and process the audio data to detect speech data 216 from the audio data 212. The audio data 212 can be retrieved in real-time or near real-time, or can be stored and retrieved at a subsequent time for processing (e.g., for batch processing, including batch processing of CRM or ERP data). As depicted in FIG. 2, a client device 220 can operate an electronic record interface 224. The electronic record interface 224 can be used to implement the electronic record 100 as described with reference to FIG. 1. The client device 220 can receive user input to be used to update the electronic record 100. While the user input may be provided through user input devices such as a keyboard and mouse, this manner of providing user input may be inefficient. As such, the client device 220 can receive an audio input (e.g., via a microphone) and provide the audio input as audio data 212 to the voice processing engine 208. The electronic record interface 224 can perform computer vision on the images displayed by the client device 220 (e.g., images displayed of the electronic record 100) to detect text and other information of the images (e.g., using various computer vision models or functions that can perform text recognition, including by matching image data with templates of text information), including to retrieve information from the electronic record 100 (this can, for example, enable the system 200 to identify the subject of the electronic record 100 to validate that the subject corresponds to the subject regarding which feedback is being received or output an error if the subject of the electronic record 100 does not correspond to the subject regarding which feedback is being received). The electronic record interface 224 can perform robotic process automation (RPA) to provide at least one of a keystroke and mouse movement to the client device 220 to input data into the electronic record 100.

As depicted in FIG. 2, at least a portion of the voice processing engine 208 can be implemented by the client device 220 (e.g., in addition to a server device remote from and communicatively coupled with the client device 220). For example, the voice processing engine 208 can be implemented by a front end application, such as a desktop application, plugin application, or mobile application, that can perform at least some processing of the audio data 212 prior to transmitting (e.g., streaming) the processed audio data 212 to another portion of the voice processing engine 208 implemented using the remote server device (e.g., a cloud-based server). The front end application can perform various processing of the audio data 212, such as filtering or compressing. The front end application can be triggered to record and perform at least a portion of the speech processing by an audio command (e.g., wake word to activate a microphone of the client device 220 to detect audio representing speech data), and the client device 220 can perform a remainder of the speech processing or transmit the partially processed speech data to the server. As such, part or all of the speech processing performed by the voice processing engine 208 can occur on the client device 220 (e.g., operating the system 200 on the edge, such as operating the voice processing engine 208 and speech model 236 on the edge), and such allocation of speech processing can be determined or modified based on security or processing capacity factors.

The system 200 can include a state monitor 228. The state monitor 228 can be implemented by the client device 220, such as by the front end application that implements at least a portion of the voice processing engine 208. The state monitor 228 can include and maintain a state data structure 232 of the electronic record interface 224. The state data structure 232 can be a data structure that indicates a state (e.g., current location) in the electronic record 100 implemented by the electronic record interface 224.

For example, the state data structure 232 can include fields indicating values of the state such as a tooth and a side of the tooth. For example, the state data structure 232 can include fields corresponding to the fields of the periodontal chart data object 104 depicted in FIG. 1, such as tooth field (e.g., the tooth field can have a value of '2') and a side field (e.g., the side field can have a value of 'buccal').

The voice processing engine 208 can receive the audio data 212 (e.g., the processed audio data 212) and generate the speech data 216 responsive to receiving the audio data 212. The voice processing engine 208 can apply various language processing systems, logic, or models to the audio data 212 to generate the speech data 216.

The voice processing engine 208 can include at least one speech model 236. The speech model 228 can be a machine learning model trained to generate the speech data 216 responsive to the audio data 212. For example, the speech model 236 can be trained using supervised learning, such as by providing, as input to the speech model 236, audio data, causing the speech model 236 to generate candidate outputs (e.g., candidate speech), comparing the candidate outputs to known values of the speech represented by the audio data, and adjusting the speech model 236 (e.g., adjusting various weights or biases of the speech model 236) responsive to the comparison to satisfy a convergence condition, such as a predetermined number of iterations or a threshold difference between the candidate outputs and the known values.

For example, the speech model 236 can be trained using audio data representing structured information and commands, such as "jump to tooth number 3." The speech model 236 can include various machine learning models, such as a neural network trained using training data including audio and vocabulary for a particular domain (e.g., dental domain).

The voice processing engine 208 can provide the audio data 212 to the at least one speech model 236 to cause the at least one speech model 236 to generate at least one phrase 240. The speech model 236 can assign a confidence score to each phrase 240; the confidence score can indicate an expectation of the accuracy of the phrase 240. The voice processing engine 208 can output the speech data 216 based on at least one the phrase 240; for example, if the speech model 236 outputs a plurality of phrases 240, the voice processing engine 208 can select one or more phrases 240, such as by comparing the confidence scores of the phrases 240 to a confidence threshold and selecting phrase(s) 240 that meet or exceed the threshold, selecting a phrase 240 having a highest confidence score, or various combinations thereof.

The voice processing engine 208 can include an intent engine (e.g., natural language processor) that can detect intents (e.g., commands and values) from the speech data 216 and/or the phrases 240. In some implementations, the voice processing engine 208 determines the at least one command from the at least one value of the at least one phrase 240. For example, particular values, numbers of values, or orderings of values may be associated with particular commands in order to determine the command (e.g., rather than determining the command from the speech data 216 itself). The voice processing engine 208 can process speech data 216 that may or may not include pauses between words, phrases, or other components of the speech data 216. For example, the speech data 216 may represent a pauseless multicommand input, in which multiple commands and/or values or represented without pauses between the commands and/or values.

The voice processing engine 208 can process speech data 216 nonsequentially, in portions (e.g., streams, chunks), or various other such formats, which can enable the overall processing of the speech data 216 to be more rapid and accurate. For example, the voice processing engine 208 can return a first phrase 240 from the speech data 216 (and assign the first phrase 240 to a corresponding field of the electronic record 100) and continue processing the speech data 216 to detect one or more second phrases 240 (e.g., subsequent to assigning the first phrase 240 to the corresponding field). For example, responsive to determining an intent of the speech data 216, the voice processing engine 208 can identify the first phrase 240 and continue to process the speech data 216 to identify the one or more second phrases 240. For example, responsive to identifying a sequence of three numbers from the speech data 216, the voice processing engine 208 can assign the three numbers to a field corresponding to the three numbers, even as additional speech data 216 (whether received before or after the three numbers) is being processed.

In some implementations, the voice processing engine 208 uses the state data structure 232 and the at least one phrase 240 to generate the speech data 216. For example, the voice processing engine 208 can apply various rules, policies, heuristics, models, or logic to the at least one phrase 240 based on the state data structure 232 to generate the speech data 216, such as to modify or update the confidence scores of the phrases 240. For example, the state data structure 232 can be used to determine an expectation of what the phrase 240 should be, as the state of the electronic record 100 represented by the state data structure 232 can indicate a likelihood of what subject data and commands are represented by the audio data 212. For example, if the state data structure 232 indicates that the state of the electronic record 100 is at tooth number 3, the voice processing engine 208 can assign a higher confidence to a particular phrase 240 that indicates subject data regarding tooth number 4 rather than tooth number 12 (e.g., based on rules or logic indicative of proximity or other spatial relationships between teeth). The state date structure 232 can be used to determine a command based on values represented by the speech data 232.

The system 200 can use the speech data 216 to update the electronic record 100 using the electronic record interface 224. For example, the system 200 can provide the speech data 216 to the client device 220 (e.g., to the front end application implemented by the client device 220) to update subject record object 208 corresponding to the subject using the electronic record interface 224.

In some implementations, the system 200 uses feedback regarding the speech data 216 to update the at least one speech model 236. The system 200 can receive feedback such as whether the speech data 216 satisfies an upper confidence threshold (e.g., indicating that the detected speech values are definitely right) or does not satisfy a lower confidence threshold (e.g., indicating that the detected speech values are definitely wrong), such as based on user input indicative of the feedback, or based on information received from the validator 248 described further herein.

The system 200 can include a record navigator 244. The record navigator 244 can be implemented using the front end application. The record navigator 244 can use the state data structure 232 and the speech data 216 to assign the speech data 216 to appropriate fields of the electronic record 100. For example, the record navigator 244 can determine which field(s) of the electronic record 100 to assign the subject data represented by the speech data 216. The record navigator 244 can include various rules, policies, heuristics, models, or logic to determine, based on the state represented by the state data structure 232 and the subject data represented by the speech data 216, which fields to assign the subject data to. For example, the record navigator 244 can include logic that if the speech data 216 includes a command of 'jump' and a location of '3' that a tab command should be entered three times in order to assign the subject data to tooth 3. As such, the front end application can write the subject data represented by the speech of the user into the electronic record 100 (e.g., into the electronic record interface 224, which can transmit the subject data to the subject database 204 to update the subject database 204).

As noted above, the electronic record 100 can be assigned at least one of structured or unstructured data. The record navigator 244 can detect context from the speech data 216 to identify (structured) fields to assign the speech data 216. The record navigator 244 can use the state monitor 228 to identify the fields to assign the speech data 216.

The system 200 can include a validator 248. The validator 248 can perform various error checking operations to improve the accuracy of assigning subject data to the electronic record 100. For example, the validator 248 can include various rules, policies, heuristics, models, or logic that can compare a command or data values indicated by the speech data 216 to expected commands or data values, and output an error responsive to the comparison not satisfying a comparison condition. For example, the validator 248 can include logic indicating that for each tooth, 3 values of pocket depths should be received, such that if the values and commands received through the speech data 216 are inconsistent with this logic, the validator 248 can output an error condition. This can improve operation of the system 200 by limiting instances in which errors may be detected subsequent to data entry (which can make it difficult to identify at which tooth or other state of the electronic record 100 the error originated from).

The system 200 can be used to perform treatment planning. For example, system 200 can retrieve, from the speech data 216, one or more treatment commands (e.g., using the at least one speech model 236 to identify the one or more treatment commands). The system 200 can use the at least one speech model 236 to identify keywords for initiating generation of a treatment plan. The system 200 can assign the one or more treatment commands to the electronic record 100. The electronic record 100 can include (or the system 200 can generate, responsive to the one or more treatment commands) a treatment plan template comprising one or more treatment plan fields, and the system 200 can use the state monitor 228 to identify treatment plan fields to which to assign the one or more treatment commands. For example, the state monitor 228 can determine, from the one or more treatment commands extracted from the speech data 216, a particular treatment plan field to assign a particular treatment command (e.g., using a model that indicates relationships between treatment plan fields and treatment commands as well as a current state of the treatment plan template). The system 200 can determine (e.g., from processing the speech data to identify the subject matter of the speech data) the treatment commands to be for charting commands to be treated, and can generate charts of existing conditions and treatments. This can enable treatment planning to be integrated into the PM, EHR, or other database itself, allowing for more rapid retrieval of the treatment plan for performing the treatment procedure and compartmentalizing the data of the treatment plan in the electronic record 100.

The system 200 can assign data associated with treatments or procedures to the electronic record 100. For example, the system 200 can process the audio data 212 to identify information such as clinical notes, procedure logs for surgical procedures or medical examinations (e.g., for various medical procedures, such as cardiological or orthopedic procedures), which can be assigned to the electronic record 100 (e.g., to particular fields for such information, or as unstructured data). The system 200 can determine a type of the information to assign the information to the electronic record 100.

The system 200 can provide feedback, such as audio feedback. For example, the system 200 can provide audio feedback using a user interface of the client device 220 to a user. The system 200 can provide the feedback based on at least one of the state and a request from the user. For example, the system 200 can use the state monitor 228 to monitor the state, and provide feedback responsive to the state corresponding to a predetermined state. For example, during a periodontal charting procedure, feedback can be provided responsive to the state being a midline state (e.g., a chime or other audio signal can be outputted responsive to a midline of the periodontal chart being crossed, allowing the user to track where they are in the procedure without needing to look at the electronic record). Responsive to a request for the feedback the system 200 can provide the feedback (e.g., using the voice processing engine 208 to detect a command requesting the feedback, such as a request to read back a most recent entry; a request to read back particular values (e.g., "what is the value of tooth number 10")). The system 200 can provide feedback to indicate an error (e.g., responsive to operation of the validator 248; responsive to determining that the state of the electronic record 100 does not match (e.g., a match score is less than a minimum match threshold) the provided speech data 216 expected to be assigned to a field corresponding to the state).

The system 200 can provide at least one report (e.g., using the client device 220). For example, the system 200 can aggregate or analyze the data of the electronic record 100 (e.g., using one or more functions, filters, rules, heuristics, or policies) to identify data elements of the electronic record 100 to include in a report. The system 200 can provide the report before, during, or after the procedure is performed on the subject. The system 200 can use a report template to assign data elements to the report. This can provide users with more digestible data, such as for use during the procedure.

The system 200 can use the client device 220 to present a training interface. The training interface can output at least one of image data (e.g., images, videos) or audio data (e.g., audio prompts) to indicate to a user how to operate the system 200 and request training inputs from the user. For example, the system 200 can output a request for a training input for a user to speak one or more particular words or phrases, and process audio data received in response to the request using various components of the system 200 (e.g., as described herein for processing audio data 212), including using the validator 248 to validate the received audio data to determine whether the user is providing inputs properly. For example, responsive to the validator 248 determining that the received audio data corresponds to the one or more particular words or phrases, the system 200 can determine that the audio data is correct (and output an indication that the audio data is correct); responsive to determining that the received audio data does not correspond to the one or more particular words or phrases, the system 200 can determine that the audio data is not correct (and output an indication that the audio data is not correct). The system 200 can use the audio data received in response to the request to train (e.g., further train) the at least one speech model 216.

The system 200 can process data using various tooth numbering systems or templates (e.g., for electronic dental records). For example, the system 200 can process data using the international tooth numbering system (1-1 to 1-8 . . . 4-1 to 4-8), as well as the US tooth numbering system (teeth numbered 1 to 32). The system 200 can process data using tooth numbering systems based on the voice processing engine 208 being trained using training data that includes speech data from each tooth numbering system. The system 200 can process the speech data 216 to detect the tooth numbering system (e.g., based on determining that a confidence that a pair of sequential numbers detected from the speech data 216 that corresponds to the international numbering system (e.g., detecting "1-1") at least one of meets a threshold or is greater than a confidence that the pair of numbers corresponds to values of a particular tooth in the US tooth numbering system. The system 200 can process data for various types of patients, such as pediatric or adult teeth systems (e.g., based on training data indicating numbering of such systems).

The system 200 can detect (e.g., using machine vision or other image processing of the electronic record 100, or responsive to user input indicating the tooth is missing) a variation of the electronic record 100 from a tooth numbering template, such as if a tooth of the subject is missing. Responsive to detecting the variation, the system 200 can process the values detected from the speech data 216 based on the variation, such as to skip assigning values to a missing tooth (e.g., responsive to detecting that tooth number 12 is missing, assign values for tooth number 11 to tooth number 11, and assign subsequent values to tooth number 13). Responsive to detecting user input indicating the variation, the system 200 can update the electronic record 100 to mark the tooth as missing.

The system 200 can process the speech data 216 and assign values to the electronic record 100 based on various orderings/paths through the teeth of the subject, such as from the buccal side of the mouth followed by lingual then lingual and back to buccal, and various other such paths. For example, the system 200 can receive user input indicating the path. The system 200 can detect the path based on maintaining a path state by the state monitor 228, which can be maintained and updated responsive to matching values indicative of the path state (e.g., sequence of tooth number values detected from the speech data 216) with expected values corresponding to the various paths (e.g., if a last buccal side tooth number is followed by a first lingual side tooth number, this can be indicative of a path from the buccal side to the lingual side). The system 200 can use the path state to modify at least one of a confidence value associated with a tooth number (or tooth value) detection by the at least one speech model 236 or the validator 248 or a threshold associated with a tooth number (or tooth value) detection by the at least one speech model 236 or the validator 248 (including if the user provides a "jump" command), enabling the system 200 to more accurately determine values to assign to the electronic record 100. The system 200 can use at least one of the path state and a tooth state maintained by the state monitor 228 to handle conditions such as moving past missing teeth and enabling a user to perform a read-back functionality (e.g., maintain a state indicative of a current tooth for which tooth values are being provided; responsive to detecting input from the speech data 216 indicating instructions to output values for a particular tooth, output the values for the particular tooth; responsive to outputting the values for the particular tooth, return to the current tooth for continuing to receive tooth values based on the at least one of the tooth state or the path state).

Figure 3:
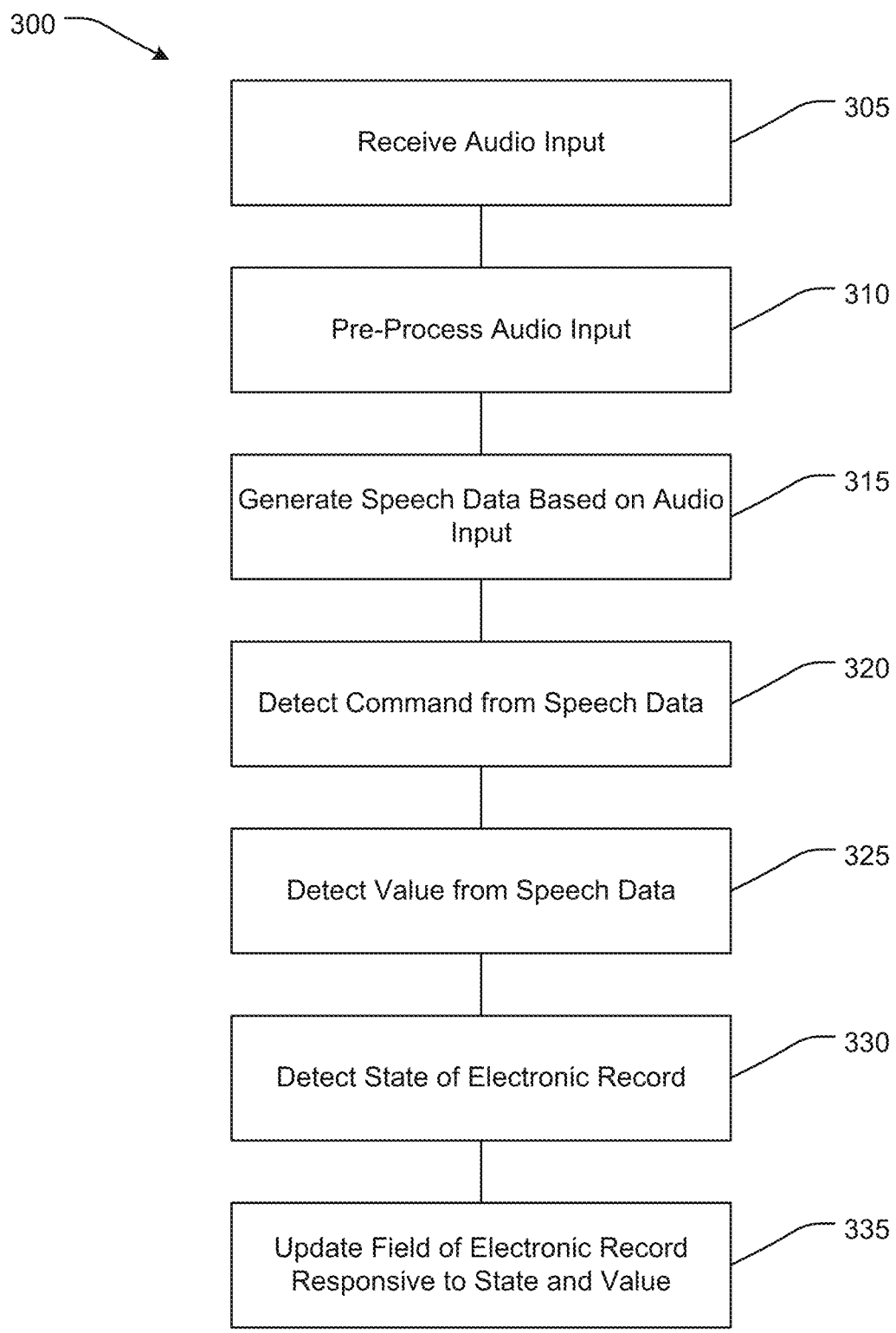
FIG. 3 depicts a flow diagram of a method for operating an electronic record voice assistant system.

FIG. 3 depicts a method 300 of operating an electronic record voice assistant system. The method 300 can be performed using various systems and devices described herein, including the electronic record 100 described with reference to FIG. 1, the system 200 described with reference to FIG. 2, and the computing device 400 and associated computing environment described with reference to FIGS. 4A and 4B. The method 300 can be used to perform real-time or batch processing of medical procedure data to accurately update an electronic record of a subject.

The method 300 can include receiving an audio input (305). The audio input can be indicative of a command. The audio input can be received via an audio input device (e.g., microphone) of a client device. The audio input can be received based on a user navigating to a webpage that connects with an electronic health record system. The audio input can represent speech that can be processed as described herein to detect a verbal command (e.g., user voice command), such as "jump to tooth number 3."

The method 300 can include pre-processing the audio input (310). For example, the audio input can be filtered or compressed for further processing. The audio input can be pre-processed by an application implemented by the client device, and transmitted to a remote device (e.g., cloud-based server) for further processing. The audio input can be transmitted as an audio stream to the remote device.

The method 300 can include generating speech data (e.g., text representative of the audio input) based on the audio input (315). The speech data can be generated by providing the audio input as an input to at least one speech model, such as a machine learning model (e.g., neural network) trained using domain-specific audio and vocabulary. The speech data can be generated by a voice processing engine implemented by the remote device (e.g., cloud-based server) to convert the audio data into text data.

The method 300 can include detecting at least one command from the speech data (320). For example, a natural language processor can be applied to the speech data to detect the at least one command. The at least one command can be representative of an intent. The at least one command can be representative of an action for selecting a field of the electronic record to which to assign subject data. The at least one command can be determined based on at least one value detected from the speech data. In some implementations, the at least one command is not detected from the speech data (e.g., the speech data may not include a command, the speech data may not be processed to detect a command, or the at least one command may be determined from the at least one value, rather than from the speech data).

The method 300 can include detecting at least one value from the speech data to be assigned to a field of the electronic record (325). The at least one value can be extracted from the speech data or from phrases determined from the speech data. For example, a natural language processor can be applied to the speech data to detect the at least one value. The at least one command (e.g., "jump") and the at least one value (e.g., "tooth 3") can form a response to be provided to the application implemented by the client device. The at least one value can represent a pauseless multicomponent (e.g., multicommand) input.

The method 300 can include detecting a state of the electronic record (330). The state can be a particular field of the electronic record that is currently selected or at which data was most recently entered. The state can be maintained in a state data structure (e.g., by the application implemented by the client device).

The method 300 can include updating a particular field of the electronic record using the at least one value, and the state (335). Updating the particular field can include updating the particular based on the at least one command, the at least one value, and the state. For example, the state can be used to identify the particular field, such as a field associated with a tooth indicated by the speech data (e.g., a tooth to move to based on the state and the at least one value, the at least one command, or a combination thereof). Updating the particular field can include causing an application that implements the electronic record on the client device to transmit the update to the electronic record to a server that maintains a subject database that includes the electronic record. The application implemented on the client device can provide inputs to the electronic record (e.g., an application that implements the electronic record) to move through a structure of the electronic record to select the particular field; for example, the application can determine to provide a tab keystroke input three times in order to jump to tooth 3. Updating the electronic record can cause the presentation of the electronic record to be updated, enabling the user to see the updates (e.g., see the value assigned to tooth 3). Updating the electronic record can include transmitting a representation of the electronic record (or values thereof) to the server to cause the server to update the subject database. The electronic record can be updated asynchronously. The electronic record can be updated in real time, or in a batch process (e.g., at the end of an examination; at regular intervals, such as hourly or daily).

Figure 4A:
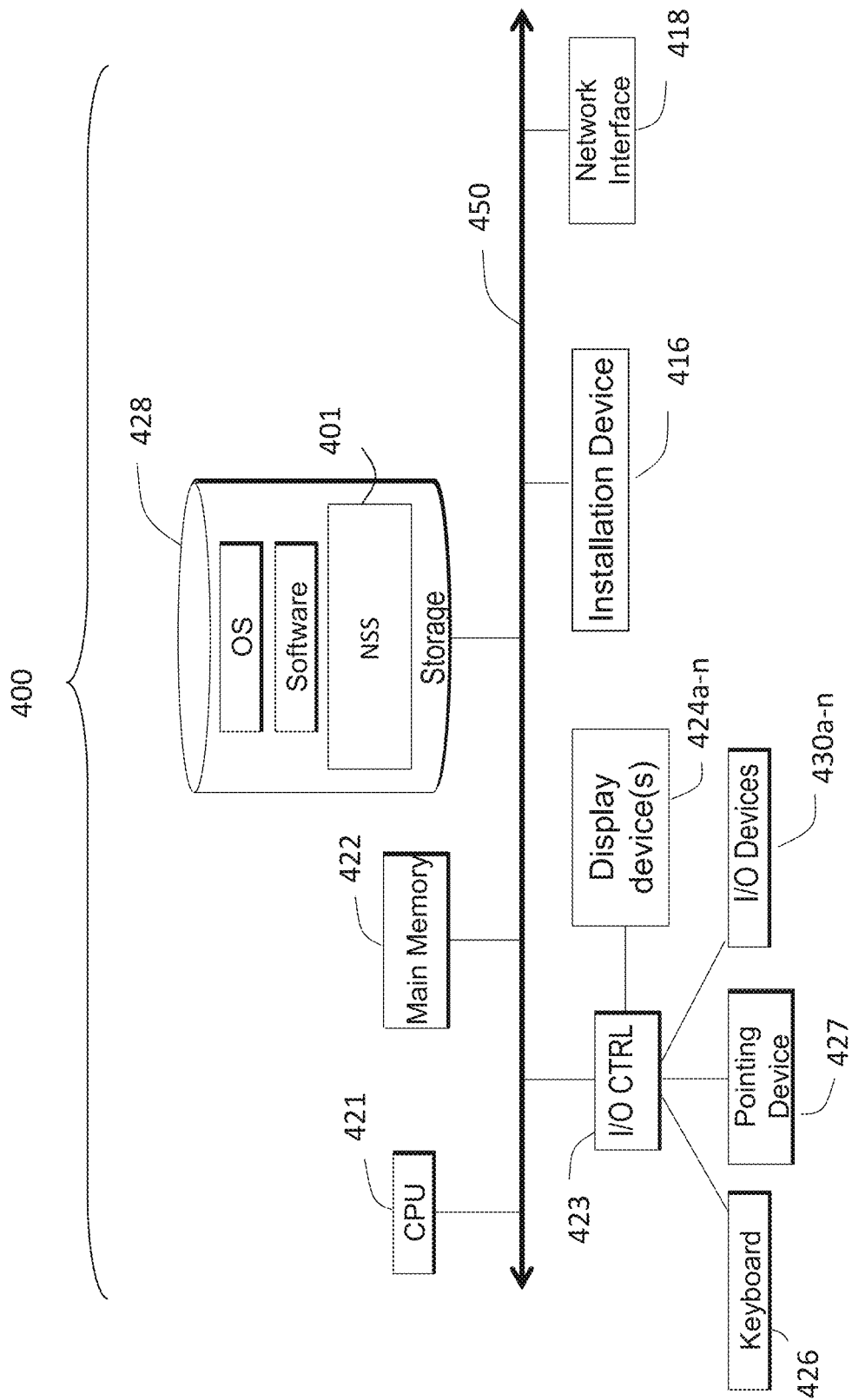
FIGS. 4A and 4B depict block diagrams of an example of a computing environment.
Figure 4B:
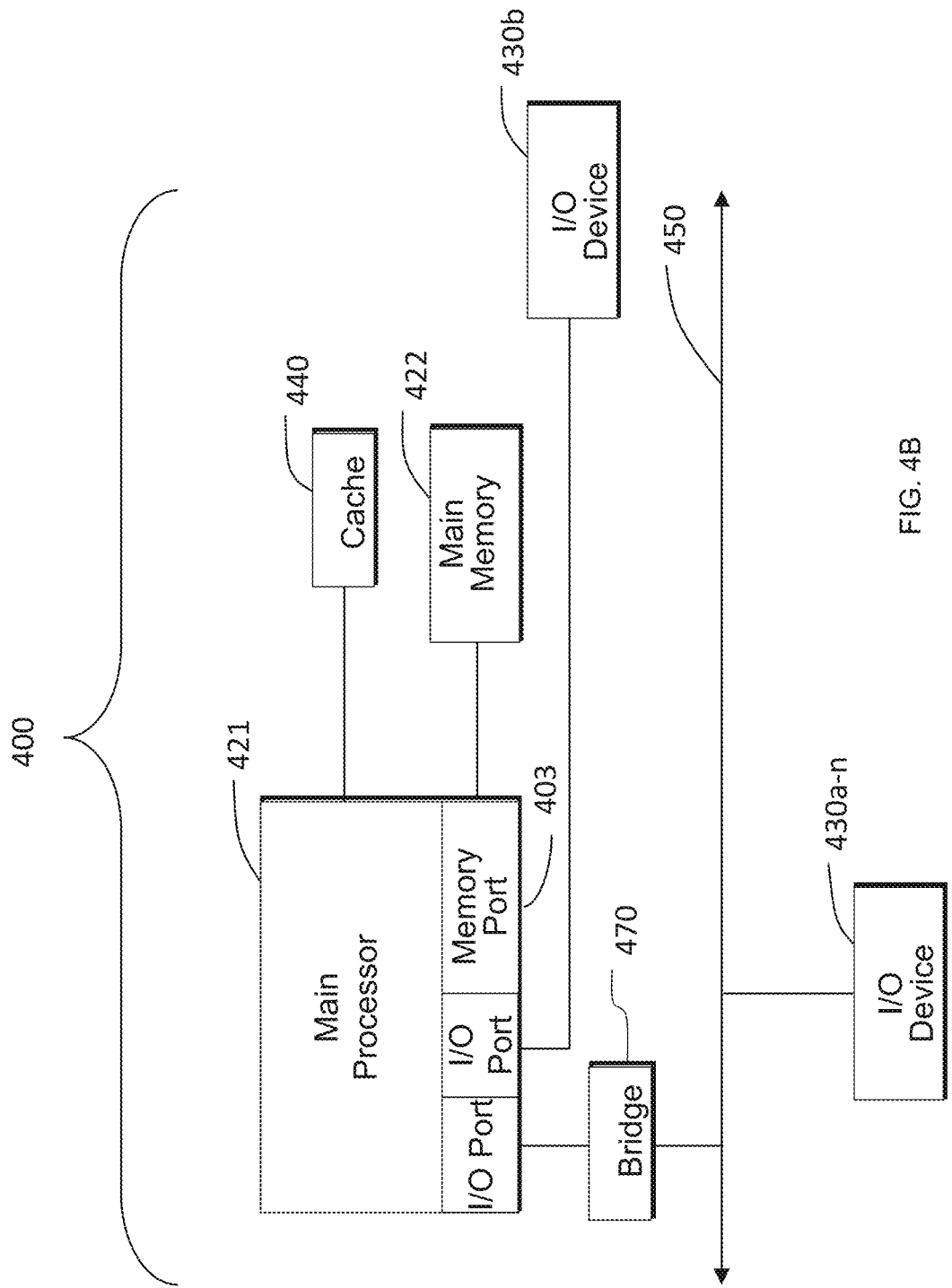

FIGS. 4A and 4B depict block diagrams of a computing device 400. As shown in FIGS. 4A and 4B, each computing device 400 includes a central processing unit 421, and a main memory unit 422. As shown in FIG. 4A, a computing device 400 can include a storage device 428, an installation device 416, a network interface 418, an I/O controller 423, display devices 424a-424n, a keyboard 426 and a pointing device 427, e.g. a mouse. The storage device 428 can include, without limitation, an operating system, software, and software of the system 200. As shown in FIG. 4B, each computing device 400 can also include additional optional elements, e.g. a memory port 403, a bridge 470, one or more input/output devices 430a-430n (generally referred to using reference numeral 430), and a cache memory 440 in communication with the central processing unit 421.

The central processing unit 421 is any logic circuitry that responds to and processes instructions fetched from the main memory unit 422. In many embodiments, the central processing unit 421 is provided by a microprocessor unit, e.g.: those manufactured by Intel Corporation of Mountain View, Calif.; those manufactured by Motorola Corporation of Schaumburg, Ill.; the ARM processor (from, e.g., ARM Holdings and manufactured by ST, TI, ATMEL, etc.) and TEGRA system on a chip (SoC) manufactured by Nvidia of Santa Clara, Calif.; the POWER7 processor, those manufactured by International Business Machines of White Plains, N.Y.; or those manufactured by Advanced Micro Devices of Sunnyvale, Calif.; or field programmable gate arrays ("FPGAs") from Altera in San Jose, Calif., Intel Corporation, Xlinix in San Jose, Calif., or MicroSemi in Aliso Viejo, Calif., etc. The computing device 400 can be based on any of these processors, or any other processor capable of operating as described herein. The central processing unit 421 can utilize instruction level parallelism, thread level parallelism, different levels of cache, and multi-core processors. A multi-core processor can include two or more processing units on a single computing component. Examples of multi-core processors include the AMD PHENOM IIX2, INTEL CORE i5 and INTEL CORE i7.

Main memory unit 422 can include one or more memory chips capable of storing data and allowing any storage location to be directly accessed by the microprocessor 421. Main memory unit 422 can be volatile and faster than storage 428 memory. Main memory units 422 can be Dynamic random access memory (DRAM) or any variants, including static random access memory (SRAM), Burst SRAM or SynchBurst SRAM (BSRAM), Fast Page Mode DRAM (FPM DRAM), Enhanced DRAM (EDRAM), Extended Data Output RAM (EDO RAM), Extended Data Output DRAM (EDO DRAM), Burst Extended Data Output DRAM (BEDO DRAM), Single Data Rate Synchronous DRAM (SDR SDRAM), Double Data Rate SDRAM (DDR SDRAM), Direct Rambus DRAM (DRDRAM), or Extreme Data Rate DRAM (XDR DRAM). In some embodiments, the main memory 422 or the storage 428 can be non-volatile; e.g., non-volatile read access memory (NVRAM), flash memory non-volatile static RAM (nvSRAM), Ferroelectric RAM (FeRAM), Magnetoresistive RAM (MRAM), Phase-change memory (PRAM), conductive-bridging RAM (CBRAM), Silicon-Oxide-Nitride-Oxide-Silicon (SONOS), Resistive RAM (RRAM), Racetrack, Nano-RAM (NRAM), or Millipede memory. The main memory 422 can be based on any of the above described memory chips, or any other available memory chips capable of operating as described herein. In the embodiment shown in FIG. 4A, the processor 421 communicates with main memory 422 via a system bus 450 (described in more detail below). FIG. 4B depicts an embodiment of a computing device 400 in which the processor communicates directly with main memory 422 via a memory port 403. For example, in FIG. 4B the main memory 422 can be DRDRAM.

FIG. 4B depicts an embodiment in which the main processor 421 communicates directly with cache memory 440 via a secondary bus, sometimes referred to as a backside bus. In other embodiments, the main processor 421 communicates with cache memory 440 using the system bus 450. Cache memory 440 typically has a faster response time than main memory 422 and is typically provided by SRAM, BSRAM, or EDRAM. In the embodiment shown in FIG. 4B, the processor 421 communicates with various I/O devices 430 via a local system bus 450. Various buses can be used to connect the central processing unit 421 to any of the I/O devices 430, including a PCI bus, a PCI-X bus, or a PCI-Express bus, or a NuBus. For embodiments in which the I/O device is a video display 424, the processor 421 can use an Advanced Graphics Port (AGP) to communicate with the display 424 or the I/O controller 423 for the display 424. FIG. 4B depicts an embodiment of a computer 400 in which the main processor 421 communicates directly with I/O device 430b or other processors 421' via HYPERTRANSPORT, RAPIDIO, or INFINIBAND communications technology. FIG. 4B also depicts an embodiment in which local busses and direct communication are mixed: the processor 421 communicates with I/O device 430a using a local interconnect bus while communicating with I/O device 430b directly.

A wide variety of I/O devices 430a-430n can be present in the computing device 400. Input devices can include keyboards, mice, trackpads, trackballs, touchpads, touch mice, multi-touch touchpads and touch mice, microphones (analog or MEMS), multi-array microphones, drawing tablets, cameras, single-lens reflex camera (SLR), digital SLR (DSLR), CMOS sensors, CCDs, accelerometers, inertial measurement units, infrared optical sensors, pressure sensors, magnetometer sensors, angular rate sensors, depth sensors, proximity sensors, ambient light sensors, gyroscopic sensors, or other sensors. Output devices can include video displays, graphical displays, speakers, headphones, inkjet printers, laser printers, and 3D printers.

Devices 430a-430n can include a combination of multiple input or output devices, including, e.g., Microsoft KINECT, Nintendo Wiimote for the WII, Nintendo WII U GAMEPAD, or Apple IPHONE. Some devices 430a-430n allow gesture recognition inputs through combining some of the inputs and outputs. Some devices 430a-430n provides for facial recognition which can be utilized as an input for different purposes including authentication and other commands. Some devices 430a-430n provides for voice recognition and inputs, including, e.g., Microsoft KINECT, SIRI for IPHONE by Apple, Google Now or Google Voice Search.

Additional devices 430a-430n have both input and output capabilities, including, e.g., haptic feedback devices, touchscreen displays, or multi-touch displays. Touchscreen, multi-touch displays, touchpads, touch mice, or other touch sensing devices can use different technologies to sense touch, including, e.g., capacitive, surface capacitive, projected capacitive touch (PCT), in-cell capacitive, resistive, infrared, waveguide, dispersive signal touch (DST), in-cell optical, surface acoustic wave (SAW), bending wave touch (BWT), or force-based sensing technologies. Some multi-touch devices can allow two or more contact points with the surface, allowing advanced functionality including, e.g., pinch, spread, rotate, scroll, or other gestures. Some touchscreen devices, including, e.g., Microsoft PIXELSENSE or Multi-Touch Collaboration Wall, can have larger surfaces, such as on a table-top or on a wall, and can also interact with other electronic devices. Some I/O devices 430a-430n, display devices 424a-424n or group of devices can be augmented reality devices. The I/O devices can be controlled by an I/O controller 421 as shown in FIG. 4A. The I/O controller 421 can control one or more I/O devices, such as, e.g., a keyboard 126 and a pointing device 427, e.g., a mouse or optical pen. Furthermore, an I/O device can also provide storage and/or an installation medium 116 for the computing device 400. In still other embodiments, the computing device 400 can provide USB connections (not shown) to receive handheld USB storage devices. In further embodiments, an I/O device 430 can be a bridge between the system bus 450 and an external communication bus, e.g. a USB bus, a SCSI bus, a FireWire bus, an Ethernet bus, a Gigabit Ethernet bus, a Fibre Channel bus, or a Thunderbolt bus.

In some embodiments, display devices 424a-424n can be connected to I/O controller 421. Display devices can include, e.g., liquid crystal displays (LCD), thin film transistor LCD (TFT-LCD), blue phase LCD, electronic papers (e-ink) displays, flexile displays, light emitting diode displays (LED), digital light processing (DLP) displays, liquid crystal on silicon (LCOS) displays, organic light-emitting diode (OLED) displays, active-matrix organic light-emitting diode (AMOLED) displays, liquid crystal laser displays, time-multiplexed optical shutter (TMOS) displays, or 3D displays. Examples of 3D displays can use, e.g. stereoscopy, polarization filters, active shutters, or autostereoscopy. Display devices 424a-424n can also be a head-mounted display (HMD). In some embodiments, display devices 424a-424n or the corresponding I/O controllers 423 can be controlled through or have hardware support for OPENGL or DIRECTX API or other graphics libraries.

In some embodiments, the computing device 400 can include or connect to multiple display devices 424a-424n, which each can be of the same or different type and/or form. As such, any of the I/O devices 430a-430n and/or the I/O controller 423 can include any type and/or form of suitable hardware, software, or combination of hardware and software to support, enable or provide for the connection and use of multiple display devices 424a-424n by the computing device 400. For example, the computing device 400 can include any type and/or form of video adapter, video card, driver, and/or library to interface, communicate, connect or otherwise use the display devices 424a-424n. In one embodiment, a video adapter can include multiple connectors to interface to multiple display devices 424a-424n. In other embodiments, the computing device 400 can include multiple video adapters, with each video adapter connected to one or more of the display devices 424a-424n. In some embodiments, any portion of the operating system of the computing device 400 can be configured for using multiple displays 424a-424n. In other embodiments, one or more of the display devices 424a-424n can be provided by one or more other computing devices 400a or 400b connected to the computing device 400, via the network 440. In some embodiments software can be designed and constructed to use another computer's display device as a second display device 424a for the computing device 400. For example, in one embodiment, an Apple iPad can connect to a computing device 400 and use the display of the device 400 as an additional display screen that can be used as an extended desktop. One ordinarily skilled in the art will recognize and appreciate the various ways and embodiments that a computing device 400 can be configured to have multiple display devices 424a-424n.

Referring again to FIG. 4A, the computing device 400 can comprise a storage device 428 (e.g. one or more hard disk drives or redundant arrays of independent disks) for storing an operating system or other related software, and for storing application software programs such as any program related to the software for the system 200. Examples of storage device 428 include, e.g., hard disk drive (HDD); optical drive including CD drive, DVD drive, or BLU-RAY drive; solid-state drive (SSD); USB flash drive; or any other device suitable for storing data. Some storage devices can include multiple volatile and non-volatile memories, including, e.g., solid state hybrid drives that combine hard disks with solid state cache. Some storage device 428 can be non-volatile, mutable, or read-only. Some storage device 428 can be internal and connect to the computing device 400 via a bus 450. Some storage device 428 can be external and connect to the computing device 400 via a I/O device 430 that provides an external bus. Some storage device 428 can connect to the computing device 400 via the network interface 418 over a network, including, e.g., the Remote Disk for MACBOOK AIR by Apple. Some client devices 400 can not require a non-volatile storage device 428 and can be thin clients or zero clients 202. Some storage device 428 can also be used as an installation device 416, and can be suitable for installing software and programs. Additionally, the operating system and the software can be run from a bootable medium, for example, a bootable CD, e.g. KNOPPIX, a bootable CD for GNU/Linux that is available as a GNU/Linux distribution from knoppix.net.

Computing device 400 can also install software or application from an application distribution platform. Examples of application distribution platforms include the App Store for iOS provided by Apple, Inc., the Mac App Store provided by Apple, Inc., GOOGLE PLAY for Android OS provided by Google Inc., Chrome Webstore for CHROME OS provided by Google Inc., and Amazon Appstore for Android OS and KINDLE FIRE provided by Amazon.com, Inc. Computing device 400 install software or applications from a source (e.g., server) maintained by a proprietor of the software or applications, such as a source independent of an application distribution platform.

Furthermore, the computing device 400 can include a network interface 418 to interface to the network 440 through a variety of connections including, but not limited to, standard telephone lines LAN or WAN links (e.g., 802.11, T1, T3, Gigabit Ethernet, Infiniband), broadband connections (e.g., ISDN, Frame Relay, ATM, Gigabit Ethernet, Ethernet-over-SONET, ADSL, VDSL, BPON, GPON, fiber optical including FiOS), wireless connections, or some combination of any or all of the above. Connections can be established using a variety of communication protocols (e.g., TCP/IP, Ethernet, ARCNET, SONET, SDH, Fiber Distributed Data Interface (FDDI), IEEE 802.11a/b/g/n/ac CDMA, GSM, WiMax and direct asynchronous connections). In one embodiment, the computing device 400 communicates with other computing devices 400' via any type and/or form of gateway or tunneling protocol e.g. Secure Socket Layer (SSL) or Transport Layer Security (TLS), or the Citrix Gateway Protocol manufactured by Citrix Systems, Inc. of Ft. Lauderdale, Fla. The network interface 118 can comprise a built-in network adapter, network interface card, PCMCIA network card, EXPRESSCARD network card, card bus network adapter, wireless network adapter, USB network adapter, modem or any other device suitable for interfacing the computing device 400 to any type of network capable of communication and performing the operations described herein.

A computing device 400 of the sort depicted in FIG. 4A can operate under the control of an operating system, which controls scheduling of tasks and access to system resources. The computing device 400 can be running any operating system such as any of the versions of the MICROSOFT WINDOWS operating systems, the different releases of the Unix and Linux operating systems, any version of the MAC OS for Macintosh computers, any embedded operating system, any real-time operating system, any open source operating system, any proprietary operating system, any operating systems for mobile computing devices, or any other operating system capable of running on the computing device and performing the operations described herein. Typical operating systems include, but are not limited to: WINDOWS 7000, WINDOWS Server 2012, WINDOWS CE, WINDOWS Phone, WINDOWS XP, WINDOWS VISTA, and WINDOWS 7, WINDOWS RT, and WINDOWS 8 all of which are manufactured by Microsoft Corporation of Redmond, Wash.; MAC OS and iOS, manufactured by Apple, Inc. of Cupertino, Calif.; and Linux, a freely-available operating system, e.g. Linux Mint distribution ("distro") or Ubuntu, distributed by Canonical Ltd. of London, United Kingdom; or Unix or other Unix-like derivative operating systems; and Android, designed by Google, of Mountain View, Calif., among others. Some operating systems, including, e.g., the CHROME OS by Google, can be used on zero clients or thin clients, including, e.g., CHROMEBOOKS.

The computer system 400 can be any workstation, telephone, desktop computer, laptop or notebook computer, netbook, ULTRABOOK, tablet, server, handheld computer, mobile telephone, smartphone or other portable telecommunications device, media playing device, a gaming system, mobile computing device, or any other type and/or form of computing, telecommunications or media device that is capable of communication. The computer system 400 has sufficient processor power and memory capacity to perform the operations described herein. In some embodiments, the computing device 400 can have different processors, operating systems, and input devices consistent with the device. The Samsung GALAXY smartphones, e.g., operate under the control of Android operating system developed by Google, Inc. GALAXY smartphones receive input via a touch interface.

In some embodiments, the computing device 400 is a gaming system. For example, the computer system 400 can comprise a PLAYSTATION 3, or PERSONAL PLAYSTATION PORTABLE (PSP), or a PLAYSTATION VITA device manufactured by the Sony Corporation of Tokyo, Japan, a NINTENDO DS, NINTENDO 3DS, NINTENDO WII, or a NINTENDO WII U device manufactured by Nintendo Co., Ltd., of Kyoto, Japan, or an XBOX 360 device manufactured by the Microsoft Corporation of Redmond, Wash., or an OCULUS RIFT or OCULUS VR device manufactured BY OCULUS VR, LLC of Menlo Park, Calif.

In some embodiments, the computing device 400 is a digital audio player such as the Apple IPOD, IPOD Touch, and IPOD NANO lines of devices, manufactured by Apple Computer of Cupertino, Calif. Some digital audio players can have other functionality, including, e.g., a gaming system or any functionality made available by an application from a digital application distribution platform. For example, the IPOD Touch can access the Apple App Store. In some embodiments, the computing device 400 is a portable media player or digital audio player supporting file formats including, but not limited to, MP3, WAV, M4A/AAC, WMA Protected AAC, AIFF, Audible audiobook, Apple Lossless audio file formats and .mov, .m4v, and .mp4 MPEG-4 (H.264/MPEG-4 AVC) video file formats.

In some embodiments, the computing device 400 is a tablet e.g. the IPAD line of devices by Apple; GALAXY TAB family of devices by Samsung; or KINDLE FIRE, by Amazon.com, Inc. of Seattle, Wash. In other embodiments, the computing device 400 is an eBook reader, e.g. the KINDLE family of devices by Amazon.com, or NOOK family of devices by Barnes & Noble, Inc. of New York City, N.Y.

In some embodiments, the communications device 400 includes a combination of devices, e.g. a smartphone combined with a digital audio player or portable media player. For example, one of these embodiments is a smartphone, e.g. the IPHONE family of smartphones manufactured by Apple, Inc.; a Samsung GALAXY family of smartphones manufactured by Samsung, Inc.; or a Motorola DROID family of smartphones. In yet another embodiment, the communications device 400 is a laptop or desktop computer equipped with a web browser and a microphone and speaker system, e.g. a telephony headset. In these embodiments, the communications devices 400 are web-enabled and can receive and initiate phone calls. In some embodiments, a laptop or desktop computer is also equipped with a webcam or other video capture device that enables video chat and video call.

In some embodiments, the status of one or more machines 400 in the network are monitored, generally as part of network management. In one of these embodiments, the status of a machine can include an identification of load information (e.g., the number of processes on the machine, CPU and memory utilization), of port information (e.g., the number of available communication ports and the port addresses), or of session status (e.g., the duration and type of processes, and whether a process is active or idle). In another of these embodiments, this information can be identified by a plurality of metrics, and the plurality of metrics can be applied at least in part towards decisions in load distribution, network traffic management, and network failure recovery as well as any aspects of operations of the present solution described herein. Aspects of the operating environments and components described above will become apparent in the context of the systems and methods disclosed herein.

All or part of the processes described herein and their various modifications (hereinafter referred to as "the processes") can be implemented, at least in part, via a computer program product, i.e., a computer program tangibly embodied in one or more tangible, physical hardware storage devices that are computer and/or machine-readable storage devices for execution by, or to control the operation of, data processing apparatus, e.g., a programmable processor, a computer, or multiple computers. A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a network.

Processors suitable for the execution of a computer program include, by way of example, both general and special purpose microprocessors, and any one or more processors of any kind of digital computer. Generally, a processor will receive instructions and data from a read-only storage area or a random access storage area or both. Elements of a computer (including a server) include one or more processors for executing instructions and one or more storage area devices for storing instructions and data. Generally, a computer will also include, or be operatively coupled to receive data from, or transfer data to, or both, one or more machine-readable storage media, such as mass storage devices for storing data, e.g., magnetic, magneto-optical disks, or optical disks.

Computer program products are stored in a tangible form on non-transitory computer readable media and non-transitory physical hardware storage devices that are suitable for embodying computer program instructions and data. These include all forms of non-volatile storage, including by way of example, semiconductor storage area devices, e.g., EPROM, EEPROM, and flash storage area devices; magnetic disks, e.g., internal hard disks or removable disks; magneto-optical disks; and CD-ROM and DVD-ROM disks and volatile computer memory, e.g., RAM such as static and dynamic RAM, as well as erasable memory, e.g., flash memory and other non-transitory devices.

The construction and arrangement of the systems and methods as shown in the various embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements may be reversed or otherwise varied and the nature or number of discrete elements or positions may be altered or varied. Accordingly, all such modifications are intended to be included within the scope of the present disclosure. The order or sequence of any process or method steps may be varied or re-sequenced. Other substitutions, modifications, changes, and omissions may be made in the design, operating conditions and arrangement of embodiments without departing from the scope of the present disclosure.

As utilized herein, the terms "approximately," "about," "substantially", and similar terms are intended to include any given ranges or numbers+/−10%. These terms include insubstantial or inconsequential modifications or alterations of the subject matter described and claimed are considered to be within the scope of the disclosure as recited in the appended claims.

It should be noted that the term "exemplary" and variations thereof, as used herein to describe various embodiments, are intended to indicate that such embodiments are possible examples, representations, or illustrations of possible embodiments (and such terms are not intended to connote that such embodiments are necessarily extraordinary or superlative examples).

The term "coupled" and variations thereof, as used herein, means the joining of two members directly or indirectly to one another. Such joining may be stationary (e.g., permanent or fixed) or moveable (e.g., removable or releasable). Such joining may be achieved with the two members coupled directly to each other, with the two members coupled to each other using a separate intervening member and any additional intermediate members coupled with one another, or with the two members coupled to each other using an intervening member that is integrally formed as a single unitary body with one of the two members. If "coupled" or variations thereof are modified by an additional term (e.g., directly coupled), the generic definition of "coupled" provided above is modified by the plain language meaning of the additional term (e.g., "directly coupled" means the joining of two members without any separate intervening member), resulting in a narrower definition than the generic definition of "coupled" provided above. Such coupling may be mechanical, electrical, or fluidic.

The term "or," as used herein, is used in its inclusive sense (and not in its exclusive sense) so that when used to connect a list of elements, the term "or" means one, some, or all of the elements in the list. Conjunctive language such as the phrase "at least one of X, Y, and Z," unless specifically stated otherwise, is understood to convey that an element may be either X, Y, Z; X and Y; X and Z; Y and Z; or X, Y, and Z (i.e., any combination of X, Y, and Z). Thus, such conjunctive language is not generally intended to imply that certain embodiments require at least one of X, at least one of Y, and at least one of Z to each be present, unless otherwise indicated.

References herein to the positions of elements (e.g., "top," "bottom," "above," "below") are merely used to describe the orientation of various elements in the FIGURES. It should be noted that the orientation of various elements may differ according to other exemplary embodiments, and that such variations are intended to be encompassed by the present disclosure.

The present disclosure contemplates methods, systems and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. Combinations of the above are also included within the scope of machine-readable media. Machine-executable instructions include, for example, instructions and data which cause a general purpose computer, special purpose computer, or special purpose processing machines to perform a certain function or group of functions.

Although the figures show a specific order of method steps, the order of the steps may differ from what is depicted. Also two or more steps may be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection steps, processing steps, comparison steps and decision steps.

What is claimed is:

1. A method of using voice commands to update electronic dental records, comprising:
   performing at least one of computer vision or text recognition, by one or more processors, on at least one of an image of an electronic record displayed by a device or a web-based interface of the electronic record to retrieve data of a periodontal chart data object, the periodontal chart data object comprising a plurality of fields, each field associated with a tooth of a subject and at least one feature of the tooth;
   receiving, by the one or more processors, audio data;
   applying, by the one or more processors, a speech model to the audio data to generate speech data including at least one value;
   determining, by the one or more processors, a command based on a particular tooth of the subject corresponding to the particular field corresponding to the state, a confidence value of the speech data based on one or more rules or logic associated with spatial relationships between teeth of the subject relative to the particular tooth, and at least one of the speech data or the at least one value; and
   determining, by the one or more processors, a command based on at least one of the speech data or the at least one value; and
   assigning, by the one or more processors, the at least one value to the at least one feature of the tooth based on the command and the state by applying a signal indicative of at least one of a keystroke or a mouse click to the device to assign the at least one value to the particular field.

2. The method of claim 1, wherein assigning, by the one or more processors, the at least one value comprises identifying the field with which the at least one feature is associated using the state.

3. The method of claim 1, further comprising updating, by the one or more processors, the state responsive to assigning the at least one value.

4. The method of claim 1, further comprising identifying, by the one or more processors, the particular field using the command.

5. The method of claim 1, wherein the one or more processors comprise a first processor operating on a client device and a second processor operating on a server device.

6. The method of claim 1, wherein generating the speech data comprises using, by the one or more processors, the particular tooth corresponding to the state as an input to the speech model.

7. The method of claim 1, wherein assigning the at least one value comprises:
   accessing, by the one or more processors, an application providing the web-based interface to the electronic record; and
   applying, by the one or more processors, the signal to the web-based interface.

8. The method of claim 1, further comprising validating, by the one or more processors, the at least one value by comparing the at least one value with an expected value and outputting an error responsive to the comparison not satisfying a comparison condition.

9. The method of claim 1, further comprising receiving, by the one or more processors, data indicative of a treatment plan, and assigning the data indicative of the treatment plan to an unstructured field of an electronic dental record that comprises the periodontal chart data object.

10. The method of claim 1, further comprising providing, by the one or more processors, a feedback output regarding the assignment of the at least one value to the at least one feature of the tooth.

11. The method of claim 1, wherein the at least one value comprises a first value and a second value subsequent to the first value, and generating the at least one value comprises generating the first value subsequent to generating the second value.

12. The method of claim 1, further comprising:
    outputting, by the one or more processors using a client device, a request for a predetermined word;
    receiving, by the one or more processors, audio data expected to represent the predetermined word; and
    outputting, by the one or more processors, an error condition responsive to determining that the audio data expected to represent the predetermined word does not match the predetermined word.

13. A system, comprising:
    one or more processors configured to:
       perform at least one of computer vision or text recognition, on at least one of an image of an electronic record displayed by a device or a web-based interface of the electronic record to retrieve data of a periodontal chart data object, the periodontal chart data object comprising a plurality of fields, each field associated with a tooth of a subject and at least one feature of the tooth;
       receive audio data;
       apply a speech model to the audio data to generate speech data including at least one value;
       determine a state of periodontal chart data object, the state corresponding to a particular field of the plurality of fields;
       determine a command based on a particular tooth of the subject corresponding to the particular field corresponding to the state, a confidence value of the speech data based on one or more rules or logic associated with spatial relationships between teeth of the subject relative to the particular tooth, and at least one of the speech data or the at least one value; and
       assign the at least one value to the at least one feature of the tooth based on the command and the state by applying a signal indicative of at least one of a keystroke or a mouse click to the device to assign the at least one value to the particular field.

14. The system of claim 13, wherein the one or more processors are configured to assign the at least one value by identifying the field with which the at least one feature is associated using the state.

15. The system of claim 13, wherein the one or more processors are configured to identify the particular field using the command.

16. The system of claim 13, wherein the one or more processors comprise a first processor operating on a client device and a second processor operating on a server device.

17. The system of claim 13, wherein the one or more processors are configured to apply a state of previously generated speech data as an input to the speech model.

18. The system of claim 13, wherein the one or more processors are configured to assign the at least one value by:
    accessing an application providing the web-based interface to the electronic record; and
    applying the signal to the web-based interface.

19. The system of claim 13, wherein the one or more processors are configured to validate the at least one value by comparing the at least one value with an expected value and outputting an error responsive to the comparison not satisfying a comparison condition.

20. A method of using voice commands to update electronic dental records, comprising:
- retrieving, by one or more processors, periodontal chart data comprising a plurality of fields, each field associated with a tooth of a subject and at least one feature of the tooth;
- identifying, by the one or more processors, a state of the periodontal chart data corresponding to a particular field of the plurality of fields;
- receiving, by the one or more processors, audio data;
- applying, by the one or more processors, a speech model to the audio data to generate a plurality of phrases from the audio data;
- determining, by the one or more processors, a confidence value of a particular phrase of the plurality of phrases based on spatial relationships corresponding to the tooth of the subject corresponding to the particular field of the periodontal chart data;
- determining, by the one or more processors, a command based on the confidence value and the state; and
- updating, by the one or more processors, the periodontal chart data based on the command.

* * * * *